United States Patent [19]

Richter et al.

[11] 4,281,668

[45] Aug. 4, 1981

[54] IMPLANTABLE CARBON ELECTRODE

[75] Inventors: Gerhard Richter, Erlangen; Erhard Weidlich, Spardorf, both of Fed. Rep. of Germany

[73] Assignee: Siemens Aktiengesellschaft, Berlin & Munich, Fed. Rep. of Germany

[21] Appl. No.: 77,622

[22] Filed: Sep. 21, 1979

[30] Foreign Application Priority Data

Sep. 28, 1978 [DE] Fed. Rep. of Germany ....... 2842318

[51] Int. Cl.³ .............................................. A61N 1/04
[52] U.S. Cl. .................................. 128/784; 128/419 P
[58] Field of Search ............................... 128/784–786, 128/419 P, 642

[56] References Cited

U.S. PATENT DOCUMENTS

| | | | |
|---|---|---|---|
| 3,722,005 | 3/1973 | Cowland | 128/642 |
| 3,981,309 | 9/1976 | Cannon | 128/786 X |
| 3,994,302 | 11/1976 | Brennen | 128/784 |
| 4,033,357 | 7/1977 | Helland et al. | 128/785 |

FOREIGN PATENT DOCUMENTS

| | | | |
|---|---|---|---|
| 2613072 | 10/1977 | Fed. Rep. of Germany | 128/419 P |
| 1219017 | 1/1971 | United Kingdom | 128/784 |

*Primary Examiner*—Lee S. Cohen
*Attorney, Agent, or Firm*—Kenyon & Kenyon

[57] ABSTRACT

The invention relates to an implantable carbon electrode. With such an electrode, the energy loss — occurring after the implantation — is to be largely avoided and also thrombus formation prevented. For this purpose the invention provides a smooth coating of hydrophilic ion conducting plastic for the electrode, comprising at least on the surface thereof, body and/or blood compatible material. The carbon electrode according to the invention serves in particular as a stimulus electrode, preferably in cardiac pacemakers.

4 Claims, No Drawings

IMPLANTABLE CARBON ELECTRODE

BACKGROUND OF THE INVENTION

The invention relates to an implantable carbon electrode, in particular a stimulus electrode.

Stimulus electrodes, for example for cardiac pacemakers, generally consist of an insulated lead-in cable and an electrode head for transmission of the stimulation impulses. Successful electrical stimulation presupposes the generation of a certain electric field strength at the excitable cell membrane. In malfunction of stimulus conduction in the heart, a stimulus electrode brings about the stimulation of a muscle fiber membrane. The stimulation spreads over the fiber and then jumps over to adjacent fibers, until in the end the entire myocardium is brought into the stimulated, i.e., contracted, state.

To activate the stimulus, an electronic cardiac pacemaker is used, consisting of an implantable electronic section including an energy supply unit and a stimulus circuit with a stimulation electrode and an indifferent electrode. During the impulse, a small capacitor is partially discharged through a stimulus circuit within 0.5 to 2 ms. During the intervals between the impulses, the capacitor is recharged from the energy supply unit, i.e, from a battery. During the impulse, the field strength required to activate the stimulus exists in the stimulable tissue in the vicinity of the electrode.

Stimulus electrodes of metals, as for example platinum or Elgiloy, cause a slow degradation of the tissue contiguous to the electrode. Within two to four weeks there forms around the electrode a layer of connective tissue not susceptible to stimulation. The result is a constant increase of the stimulus threshold. The electrode, therefore, becomes apparently greater, and in order to restore the necessary field strength at the limit of the stimulable tissue a stronger current, and accordingly a higher voltage, is required. At the same time, however, the ohmic loss at the constriction resistance of the stimulus electrode and the polarization losses due to electrochemical reactions at the electrode surface increase.

The body's defense reaction, which manifests itself in the formation of a non-stimulable tissue layer, is generally regarded as being caused by chemical and electrochemical processes, for example, the electrochemical corrosion of the electrode and the electrolytic decomposition of the body fluid as well as electrolytic reduction or oxidation reactions or shifts of the pH value connected with these reactions. To avoid such reactions with the consequences connected therewith, one strives to use electrode materials as inert as possible, which neither corrode nor cause electrocatalytic reactions. Thus the use of spectrally pure graphite and carbon as electrode material for stimulus electrodes is known.

In addition, the use of glass carbon (vitreous carbon) and pyrocarbon (pyrolytic carbon) as material for implantable electrodes or their electrode head is known (cf. U.S. Pat. Application Ser. Nos. 778,213 and 778,214, filed Mar. 16, 1977, now abandoned). Glass carbon and pyrocarbon, in fact, have proved to be particularly compatible with the body, because they are evidently sufficiently inert. However, the smooth electrodes cause relatively high polarization losses. These losses can be avoided if the electrodes are superficially activated, i.e., are microporously roughened by surface oxidation.

Implanted in the skeletal muscle of cats, such carbon electrodes show very low stimulus threshold currents and voltages, and also in long-term tests the stimulus threshold hardly increases. If the same electrodes are implanted in the heart of dogs, on the other hand, even though the initial stimulus energy remains very low, the stimulus threshold increases in time. Presumably the difference derives from the lower and rarer activity of the skeletal muscle as compared with the cardiac muscle. In addition, difficulties arise when it is not possible to place the electrode in the heart quickly. Upon prolonged stay in the blood stream, in fact, clots apparently form at the microporous surface which then, upon final implantation of the electrode in the heart, prevent the electrode surface from coming in direct contact with the stimulable tissue. In this manner a higher initial stimulus threshold is obtained, which is then reflected also in a higher long-term stimulus threshold.

It is the object of the invention to avoid, to the extent possible, the energy losses occurring with implantable carbon electrodes due to the post-operative stimulus threshold increase in the heart muscle, and also to prevent thrombus formation at the electrode surface, which would lead to increased initial and long-term stimulus thresholds.

According to the invention, this is achieved in that the electrode surface has a smooth coating of hydrophilic, ion-conducting plastic, and that at least the surface of the plastic coating consists of body- and/or blood-compatible material.

The coating of hydrophilic, ion-conducting plastic according to the invention results in the coverage and equalization of the microporous surface of the implantable electrode. The coating of a smooth, water-containing plastic layer improves the compatibility, reduces friction with the muscle tissue, and at the same time prevents thrombus formation. In this way the post-operative stimulus threshold increase is limited and low long-term stimulus threshold energies are obtained.

Because of the required long-term stability under physiological conditions, the coating material utilized must be correspondingly stable in physiologic ambient. In addition, it is advantageous if the material can be introduced into the pores of the electrode surface in liquid or dissolved form and be consolidated therein.

Accordingly, hydrogels and ion exchangers preferably are used as coating material for the implantable electrode according to the invention. By hydrogels are here understood gels consisting of hydrophilic, water-containing polymers (plastics). The coatings are advantageously produced by polymerization of these materials in the pore structure of the electrode.

A preferred hydrogel is produced by polymerization from 2-hydroxyethylmethacrylate as the chain former and about 5 wt.% glycol dimethacrylate as the bridge former (for crosslinking) with a usual initiator, e.g., ammonium persulfate or benzoyl peroxide. As a solvent, a glycol-water mixture or dimethyl formamide may be used.

Suitable ion exchangers are produced for example from vinyl compounds with ionizable groups, such as styrene sulfonic acid or methacrylic acid, using as a crosslinking agent in particular divinyl benzene. In principle, however, all hydrophilic, ionizable monomers are suitable for polymerization; they can be used also in mixture with one another and with hydrophobic monomers. The quantity of solvent depends on the desired degree of swelling or the desired water content and on the electrolytic conductivity of the polymerized plastic. The water content is generally chosen between 30 and 90%. A high water content is desirable in order to obtain high ion mobility in the swollen polymer. On the other hand, a lower degree of swelling is advantageous for mechanical strength. A water content of about 40 to 50% has therefore proved particularly advantageous.

Besides the hydrophilic monomers referred to, other monomers known in the art may be employed for the production of the electrode coating. Thus, for example, hydrogels on a glycerin methacrylate base can be used for the electrode according to the invention. Suitable ion exchangers can be produced not only from acrylic and methacrylic acid, but also from all other acid monomers. The use of basic monomers, such as vinyl pyridine or vinyl pyrrolidone, is not appropriate because positively charged surfaces normally promote thrombus formation. In case an electrode is to be coated with a corresponding polymer with basic groups, it is expedient, therefore, to coat or to cover the outer surface further with a neutral or a negatively charged polymer or with a respective membrane. To improve the body and blood compatibility, heparin may be fixed—in a manner known in itself—on the plastic layer of the electrode or incorporated in the plastic itself.

Preference is given in the electrode according to the invention to main valence-linked and cross-linked hydrophilic polymers because of their stability toward the body fluid. However, in principle, other hydrophilic polymers may also be utilized. As an example there may be mentioned here the hydrophilic polyurethanes, which lend themselves because of their good body and blood compatibility.

The electrode according to the invention may have the form of a solid carbon electrode, but carbon fiber bundles as well as carbon felts or carbon fabrics and foam carbon may also be advantageously used; such materials are then coated or impregnated with plastic. As carbon material is preferably employed glass carbon or pyro-carbon for the electrode of the invention, at least the surface of the electrode head consisting of such material. Advantageously the surfaces of such electrodes are activated, i.e., provided with a microporous structure, the pore diameter being in the range of about 0.5 nm (5 ang). Activation, i.e., roughening of the surface, can be effected advantageously by tempering in air at about 500° C.

Implantable electrodes of activated glass or pyrocarbon according to the invention, provided with a plastic coating, have various distinguishing features:

Avoidance of Faraday electrode processes and of postoperative stimulus threshold increase by use of body compatible carbon as the electrode material;

Reduction of energy losses due to electrode polarization by roughening of the electrode surface;

Prevention of thrombus formation at the rough electrode surface by the plastic coating; thrombus formation occurs in particular upon intravenous introduction of the electrode into the heart, the thrombotic depositions then obstructing direct and uniform contact of the electrode with the stimulable myocardium tissue.

With the electrode according to the invention a considerable reduction of the stimulus energy can be obtained. Thereby, at equal capacity of the energy source, in particular that of a cardiac pacemaker, a longer life is achieved or, respectively, it becomes possible to reduce the size of the battery and pacemaker. Small cardiac pacemakers result in an improvement for the patient and facilitate the surgery required for their implantation. The electrode of the invention can be used not only as a stimulus electrode for cardiac pacemakers but also as a stimulation electrode for muscle and nerve stimulation.

The invention will now be further explained with reference to the following examples.

EXAMPLE 1 (Comparison example)

A hemispherical glass carbon electrode (surface: 0.09 $cm^2$) is tempered in air for half an hour at about 500° C. and thereby activated. There forms a thin, microporous surface layer of a thickness of about 50 microns; the roughness factor is about 1000. The capacitance of such an electrode reaches 480 $\mu F$. For contacting, a cylindrical projection of the electrode is glued to an Elgiloy coil by means of a silver-containing conductive epoxy resin, and for insulation the coil is coated with a silicone hose. After treatment with gaseous ethylene oxide at room temperature for sterilization, the electrode is implanted in the heart of a dog, observing the longterm stimulus threshold with a Vario Pacemaker (Siemens-Elema AB). When a permanent magnet is placed on, the vario pacemaker changes its voltage intermittently in 15 steps by one fifteenth of the maximum voltage each time. The stimulus threshold is determined from the number of effective impulses which can be seen in the EKG. It is found to be 525 mV. The initial current stimulus threshold is 0.18 mA.

In another implantation experiment it was at first not possible to introduce the electrode into the heart, so that it remained at first in the vein for about 30 minutes before it had reached its final position in the heart. In this case the initial current stimulus threshold was 0.38 mA and the long-term stimulus threshold rose to 1.05 V.

EXAMPLE 2

A glass carbon electrode which—as in Example 1—had been activated by tempering in air and had then been contacted and insulated, is immersed in a commercial hydrophilic marine varnish mixed with catalyst (hydrogel on 2hydroxy-ethylmethacrylate base; chromium salt as catalyst) and then dried. The electrode is then placed in a common salt solution and heated to 160° C. for 20 minutes in a fused ampoule for sterilization. After implantation it shows a long-term stimulus threshold of 350 mV.

EXAMPLE 3

An electrode activated, contacted and insulated as in Example 1 is placed with exclusion of oxygen in 1 ml of a mixture of 4.4 ml water, 13 ml 2-hydroxy-ethylmethacrylate, 0.33 ml tetra-ethylene glycol dimethyacrylate, and 3 ml of a 5% solution of potassium peroxidisulate, heated to 80° C. and taken out at incipient polymerization and further maintained over the solution at a temperature of 80° C. The electrode is then sterilized for 3 hours in ethylene oxide gas and subsequently implanted. Although this electrode with a hydrogel coating was purposely left lying free in the blood of the heart chamber for 5 minutes before it was pushed forward into the tip of the heart, the initial current stimulus threshold remained at 0.21 mA and the long-term stimulus threshold voltage below 350 mV.

EXAMPLE 4

An electrode of pyrocarbon, which had been activated, contacted and insulated according to Example 1, is placed in a mixture containing 20 wt. % methacrylic acid, 77.5 wt. % methacrylic acid butyl ester, 2 wt. % glycol dimethacrylate and 0.5 wt. % benzoyl peroxide. This mixture is then heated to about 80° C., and at incipient polymerization the electrode is taken out and further hardened at 60° C. for 8 hours. The electrode is then boiled in a phosphate buffer solution having a pH value of 7.4, sterilized with gaseous ethylene oxide, and implanted. The long-term stimulus threshold of such an electrode with a coating of an ion exchange type copolymer remains below 350 mV.

EXAMPLE 5

A carbon fiber bundle of a diameter of about 2 mm is gold-plated at one end over a length of 0.5 cm, surrounded with an Elgiloy coil, and spot welded therewith. Then the fiber bundle is cut off 1 cm behind the gold-plated point and immersed in concentrated sulfuric acid heated to about 330° C. for 2 minutes for activation at the free end. The adhering sulfuric acid is washed out thoroughly with distilled water, and the electrode is then immersed in a phosphate buffer solution of a pH value of 7.4 for neutralization. The Elgiloy coil and the carbon fiber bundle are thereafter coated with a fitting silicone hose to the extent that 2.5 mm of the fiber bundle protrude. The free end of the fiber bundle is then immersed in 1 ml of a mixture of 4.4 ml water, 0.1 g heparin as sodium salt, 13 ml 2-hydroxyethyl-methacrylate, 0.33 ml tetra-ethylene glycol dimethacrylate and 3 ml of a 5% solution of potassium peroxidisulfate, heated for 5 minutes to 80° C., taken out of the mixture and scraped off to the extent that the fiber ends are just barely covered with plastic. Then the polymerization is brought to an end in a closed vessel over the respective mixture at 80° C. in 5 hours. Thereafter the electrode is sterilized with gaseous ethylene oxide and introduced into the heart of a dog. The long-term voltage stimulus threshold remains under 350 mV.

What is claimed is:

1. An implantable carbon electrode comprised of an electrically conductive electrode body and an electrode head, said electrode adapted for contact with an insulated lead-in cable, wherein at least the surface of said electrode head comprises a material selected from the group consisting of glass carbon and pyrolytic carbon which has been superficially activated to present a microporous surface, and wherein the surface of said electrode is provided with a smooth coating consisting of a hydrophilic, ion-conducting plastic having at least a surface thereof comprised of a body and/or blood compatible material.

2. The implantable carbon electrode of claim 1 wherein said coating consists of a hydrogel.

3. The implantable electrode of claim 1 wherein said coating consists of an ion exchange material.

4. The implantable carbon electrode of claim 1 wherein said electrode comprises a carbon fiber bundle.

* * * * *